United States Patent
Seguin et al.

(10) Patent No.: US 9,237,886 B2
(45) Date of Patent: Jan. 19, 2016

(54) IMPLANT FOR TREATMENT OF A HEART VALVE, IN PARTICULAR A MITRAL VALVE, MATERIAL INCLUDING SUCH AN IMPLANT, AND MATERIAL FOR INSERTION THEREOF

(75) Inventors: Jacques Seguin, London (GB); Than Nguyen, Irvine, CA (US); Bruno Lecointe, Rueil Malmaison (FR)

(73) Assignee: Medtronic, Inc., Minneapolis, MN (US)

( * ) Notice: Subject to any disclaimer, the term of this patent is extended or adjusted under 35 U.S.C. 154(b) by 1225 days.

(21) Appl. No.: 12/596,343

(22) PCT Filed: Apr. 14, 2008

(86) PCT No.: PCT/IB2008/000971
§ 371 (c)(1),
(2), (4) Date: Jul. 21, 2010

(87) PCT Pub. No.: WO2008/129405
PCT Pub. Date: Oct. 30, 2008

(65) Prior Publication Data
US 2010/0292785 A1 Nov. 18, 2010

Related U.S. Application Data

(60) Provisional application No. 60/907,907, filed on Apr. 20, 2007.

(30) Foreign Application Priority Data

Apr. 20, 2007 (FR) .................................... 07 02889

(51) Int. Cl.
*A61F 2/24* (2006.01)
*A61B 17/04* (2006.01)
*A61B 17/00* (2006.01)

(52) U.S. Cl.
CPC ....... *A61B 17/0401* (2013.01); *A61B 17/00234* (2013.01); *A61F 2/2442* (2013.01); *A61B 2017/0441* (2013.01); *A61B 2017/0464* (2013.01); *A61F 2002/249* (2013.01)

(58) Field of Classification Search
CPC ..................... A61B 17/00234; A61B 17/0401; A61B 2017/0441; A61B 2017/0464; A61F 2/2442; A61F 2002/249
See application file for complete search history.

(56) References Cited

U.S. PATENT DOCUMENTS 3,216,424 A * 11/1965 Chardack ....................... 607/129
3,243,755 A * 3/1966 Johnston ....................... 439/825

(Continued)

FOREIGN PATENT DOCUMENTS

CN 2007-100074433 1/2007
DE 3640745 6/1987

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Gregory Anderson
*Assistant Examiner* — Son Dang

(57) ABSTRACT

This implant (1) is formed by a helically wound wire (2). According to the invention, it has dimensions such that it is able to be screwed into the wall of the annulus (103) and/or into the cardiac wall (101) adjoining this annulus (103) such that a portion of said annulus (103) and/or of said wall (101) is located in the perimeter of the implant (1); and it comprises at least one first coil able, during said screwing of the implant (1), to insert itself into said wall while having a first dimension and at least one second coil having a second dimension, or adopting this second dimension after implantation, said second dimension being smaller than the first dimension such that the implant (1), once inserted, enables contraction of said wall portion located in the perimeter of this implant (1).

11 Claims, 8 Drawing Sheets

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,416,534 A * | 12/1968 | Quinn | 607/131 |
| 3,540,431 A | 11/1970 | Mobin-Uddin | |
| 3,587,115 A | 6/1971 | Shiley | |
| 3,628,535 A | 12/1971 | Ostrowsky et al. | |
| 3,642,004 A | 2/1972 | Osthagen et al. | |
| 3,653,171 A * | 4/1972 | Galloway | 52/521 |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,000,745 A * | 1/1977 | Goldberg | 607/127 |
| 4,035,849 A | 7/1977 | Angell et al. | |
| 4,056,854 A | 11/1977 | Boretos et al. | |
| 4,106,129 A | 8/1978 | Carpentier et al. | |
| 4,149,528 A * | 4/1979 | Murphy | 600/376 |
| 4,180,080 A * | 12/1979 | Murphy | 600/375 |
| 4,222,126 A | 9/1980 | Boretos et al. | |
| 4,233,690 A | 11/1980 | Akins | |
| 4,265,694 A | 5/1981 | Boretos | |
| 4,282,885 A * | 8/1981 | Bisping | 607/127 |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,425,908 A | 1/1984 | Simon | |
| 4,470,157 A | 9/1984 | Love | |
| 4,501,030 A | 2/1985 | Lane | |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,612,011 A | 9/1986 | Kautzky | |
| 4,647,283 A | 3/1987 | Carpentier et al. | |
| 4,648,881 A | 3/1987 | Carpentier et al. | |
| 4,655,771 A | 4/1987 | Wallsten | |
| 4,662,885 A | 5/1987 | DiPisa, Jr. | |
| 4,665,906 A | 5/1987 | Jervis | |
| 4,681,908 A | 7/1987 | Broderick et al. | |
| 4,710,192 A | 12/1987 | Liotta et al. | |
| 4,733,665 A | 3/1988 | Palmaz | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,819,751 A | 4/1989 | Shimada et al. | |
| 4,832,051 A * | 5/1989 | Jarvik et al. | 607/116 |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,954,126 A | 9/1990 | Wallsten | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,002,559 A | 3/1991 | Tower | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,061,273 A | 10/1991 | Yock | |
| 5,076,285 A * | 12/1991 | Hess et al. | 607/127 |
| 5,085,635 A | 2/1992 | Cragg | |
| 5,089,015 A | 2/1992 | Ross | |
| 5,152,771 A | 10/1992 | Sabbaghian et al. | |
| 5,161,547 A | 11/1992 | Tower | |
| 5,163,953 A | 11/1992 | Vince | |
| 5,167,628 A | 12/1992 | Boyles | |
| 5,217,483 A | 6/1993 | Tower | |
| 5,232,445 A | 8/1993 | Bonzel | |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,415,633 A | 5/1995 | Lazarus et al. | |
| 5,431,676 A | 7/1995 | Dubrul et al. | |
| 5,443,446 A | 8/1995 | Shturman | |
| 5,449,384 A | 9/1995 | Johnson | |
| 5,480,424 A | 1/1996 | Cox | |
| 5,489,294 A | 2/1996 | McVenes et al. | |
| 5,489,297 A | 2/1996 | Duran | |
| 5,496,346 A | 3/1996 | Horzewski et al. | |
| 5,500,014 A | 3/1996 | Quijano et al. | |
| 5,507,767 A | 4/1996 | Maeda et al. | |
| 5,545,209 A | 8/1996 | Roberts et al. | |
| 5,545,211 A | 8/1996 | An et al. | |
| 5,545,214 A | 8/1996 | Stevens | |
| 5,554,185 A | 9/1996 | Block et al. | |
| 5,575,818 A | 11/1996 | Pinchuk | |
| 5,580,922 A | 12/1996 | Park et al. | |
| 5,591,195 A | 1/1997 | Taheri et al. | |
| 5,609,626 A | 3/1997 | Quijano et al. | |
| 5,645,559 A | 7/1997 | Hachtman et al. | |
| 5,665,115 A | 9/1997 | Cragg | |
| 5,667,523 A | 9/1997 | Bynon et al. | |
| 5,674,277 A | 10/1997 | Freitag | |
| 5,695,498 A | 12/1997 | Tower | |
| 5,702,368 A | 12/1997 | Stevens et al. | |
| 5,713,953 A | 2/1998 | Vallana et al. | |
| 5,716,390 A * | 2/1998 | Li | 607/127 |
| 5,716,391 A * | 2/1998 | Grandjean | 607/127 |
| 5,716,417 A | 2/1998 | Girard et al. | |
| 5,746,709 A | 5/1998 | Rom et al. | |
| 5,749,890 A | 5/1998 | Shaknovich | |
| 5,766,151 A | 6/1998 | Valley et al. | |
| 5,782,809 A | 7/1998 | Umeno et al. | |
| 5,800,456 A | 9/1998 | Maeda et al. | |
| 5,800,508 A | 9/1998 | Goicoechea et al. | |
| 5,817,126 A | 10/1998 | Imran | |
| 5,824,041 A | 10/1998 | Lenker | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,837,007 A * | 11/1998 | Altman et al. | 607/127 |
| 5,840,081 A | 11/1998 | Andersen et al. | |
| 5,843,158 A | 12/1998 | Lenker et al. | |
| 5,851,232 A | 12/1998 | Lois | |
| 5,855,597 A | 1/1999 | Jayaraman | |
| 5,855,601 A | 1/1999 | Bessler et al. | |
| 5,860,966 A | 1/1999 | Tower | |
| 5,861,028 A | 1/1999 | Angell | |
| 5,868,783 A | 2/1999 | Tower | |
| 5,871,531 A * | 2/1999 | Struble | 607/126 |
| 5,876,448 A | 3/1999 | Thompson et al. | |
| 5,888,201 A | 3/1999 | Stinson et al. | |
| 5,891,191 A | 4/1999 | Stinson | |
| 5,906,619 A | 5/1999 | Olson et al. | |
| 5,907,893 A | 6/1999 | Zadno-Azizi et al. | |
| 5,913,842 A | 6/1999 | Boyd et al. | |
| 5,925,063 A | 7/1999 | Khosravi | |
| 5,944,738 A | 8/1999 | Amplatz et al. | |
| 5,957,949 A | 9/1999 | Leonhardt et al. | |
| 5,968,068 A | 10/1999 | Dehdashtian et al. | |

(56) References Cited

U.S. PATENT DOCUMENTS

| | | | |
|---|---|---|---|
| 5,984,957 | A | 11/1999 | Laptewicz, Jr. et al. |
| 5,997,573 | A | 12/1999 | Quijano et al. |
| 6,022,370 | A | 2/2000 | Tower |
| 6,027,525 | A | 2/2000 | Suh et al. |
| 6,029,671 | A | 2/2000 | Stevens et al. |
| 6,042,589 | A | 3/2000 | Marianne |
| 6,042,598 | A | 3/2000 | Tsugita et al. |
| 6,042,607 | A | 3/2000 | Williamson, IV |
| 6,051,014 | A | 4/2000 | Jang |
| 6,059,809 | A | 5/2000 | Amor et al. |
| 6,110,201 | A | 8/2000 | Quijano et al. |
| 6,146,366 | A | 11/2000 | Schachar |
| 6,159,239 | A | 12/2000 | Greenhalgh |
| 6,162,208 | A | 12/2000 | Hipps |
| 6,162,245 | A | 12/2000 | Jayaraman |
| 6,168,614 | B1 | 1/2001 | Andersen et al. |
| 6,171,335 | B1 | 1/2001 | Wheatley et al. |
| 6,200,336 | B1 | 3/2001 | Pavcnik et al. |
| 6,203,550 | B1 | 3/2001 | Olson |
| 6,210,408 | B1 | 4/2001 | Chandrasekaran et al. |
| 6,218,662 | B1 | 4/2001 | Tchakarov et al. |
| 6,221,006 | B1 | 4/2001 | Dubrul et al. |
| 6,221,091 | B1 | 4/2001 | Khosravi |
| 6,241,757 | B1 | 6/2001 | An et al. |
| 6,245,102 | B1 | 6/2001 | Jayaraman |
| 6,248,116 | B1 | 6/2001 | Chevilon et al. |
| 6,258,114 | B1 | 7/2001 | Konya et al. |
| 6,258,115 | B1 | 7/2001 | Dubrul |
| 6,258,120 | B1 | 7/2001 | McKenzie et al. |
| 6,277,555 | B1 | 8/2001 | Duran et al. |
| 6,299,637 | B1 | 10/2001 | Shaolia et al. |
| 6,302,906 | B1 | 10/2001 | Goicoechea et al. |
| 6,309,382 | B1 | 10/2001 | Garrison et al. |
| 6,309,417 | B1 | 10/2001 | Spence et al. |
| 6,338,735 | B1 | 1/2002 | Stevens |
| 6,348,063 | B1 | 2/2002 | Yassour et al. |
| 6,350,277 | B1 | 2/2002 | Kocur |
| 6,352,708 | B1 | 3/2002 | Duran et al. |
| 6,371,970 | B1 | 4/2002 | Khosravi et al. |
| 6,371,983 | B1 | 4/2002 | Lane |
| 6,379,383 | B1 | 4/2002 | Palmaz et al. |
| 6,380,457 | B1 | 4/2002 | Yurek et al. |
| 6,398,807 | B1 | 6/2002 | Chouinard et al. |
| 6,409,750 | B1 | 6/2002 | Hyodoh et al. |
| 6,425,916 | B1 | 7/2002 | Garrison et al. |
| 6,440,164 | B1 | 8/2002 | DiMatteo et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,303 | B1 | 10/2002 | Amplatz et al. |
| 6,475,239 | B1 | 11/2002 | Campbell et al. |
| 6,482,228 | B1 | 11/2002 | Norred |
| 6,488,704 | B1 | 12/2002 | Connelly et al. |
| 6,494,909 | B2 | 12/2002 | Greenhalgh |
| 6,503,272 | B2 | 1/2003 | Duerig et al. |
| 6,508,833 | B2 | 1/2003 | Pavcnik et al. |
| 6,527,800 | B1 | 3/2003 | McGuckin, Jr. et al. |
| 6,530,949 | B2 | 3/2003 | Konya et al. |
| 6,530,952 | B2 | 3/2003 | Vesely |
| 6,562,031 | B2 | 5/2003 | Chandrasekaran et al. |
| 6,562,058 | B2 | 5/2003 | Seguin et al. |
| 6,569,196 | B1 | 5/2003 | Vesely |
| 6,585,758 | B1 | 7/2003 | Chouinard et al. |
| 6,592,546 | B1 | 7/2003 | Barbut et al. |
| 6,605,112 | B1 | 8/2003 | Moll et al. |
| 6,613,077 | B2 | 9/2003 | Gilligan et al. |
| 6,622,604 | B1 | 9/2003 | Chouinard et al. |
| 6,635,068 | B1 | 10/2003 | Dubrul et al. |
| 6,652,571 | B1 | 11/2003 | White et al. |
| 6,652,578 | B2 | 11/2003 | Bailey et al. |
| 6,656,213 | B2 | 12/2003 | Solem |
| 6,663,663 | B2 | 12/2003 | Kim et al. |
| 6,669,724 | B2 | 12/2003 | Park et al. |
| 6,673,089 | B1 | 1/2004 | Yassour et al. |
| 6,673,109 | B2 | 1/2004 | Cox |
| 6,676,698 | B2 | 1/2004 | McGuckin, Jr. et al. |
| 6,682,558 | B2 | 1/2004 | Tu et al. |
| 6,682,559 | B2 | 1/2004 | Myers et al. |
| 6,685,739 | B2 | 2/2004 | DiMatteo et al. |
| 6,689,144 | B2 | 2/2004 | Gerberding |
| 6,689,164 | B1 | 2/2004 | Seguin |
| 6,692,512 | B2 | 2/2004 | Jang |
| 6,692,513 | B2 | 2/2004 | Streeter et al. |
| 6,695,878 | B2 | 2/2004 | McGuckin, Jr. et al. |
| 6,702,851 | B1 | 3/2004 | Chinn et al. |
| 6,719,789 | B2 | 4/2004 | Cox |
| 6,730,118 | B2 | 5/2004 | Spenser et al. |
| 6,730,377 | B2 | 5/2004 | Wang |
| 6,733,525 | B2 | 5/2004 | Yang et al. |
| 6,736,846 | B2 | 5/2004 | Cox |
| 6,752,828 | B2 | 6/2004 | Thornton |
| 6,758,855 | B2 | 7/2004 | Fulton, III et al. |
| 6,769,434 | B2 | 8/2004 | Liddicoat et al. |
| 6,786,925 | B1 | 9/2004 | Schoon |
| 6,790,229 | B1 | 9/2004 | Berreklouw |
| 6,792,979 | B2 | 9/2004 | Konya et al. |
| 6,797,002 | B2 | 9/2004 | Spence |
| 6,821,297 | B2 | 11/2004 | Snyders |
| 6,830,575 | B2 | 12/2004 | Stenzel et al. |
| 6,830,584 | B1 | 12/2004 | Seguin |
| 6,830,585 | B1 | 12/2004 | Artof |
| 6,846,325 | B2 | 1/2005 | Liddicoat |
| 6,866,650 | B2 | 3/2005 | Stevens |
| 6,872,223 | B2 | 3/2005 | Roberts |
| 6,875,231 | B2 | 4/2005 | Anduiza et al. |
| 6,883,522 | B2 | 4/2005 | Spence et al. |
| 6,887,266 | B2 | 5/2005 | Williams et al. |
| 6,890,330 | B2 | 5/2005 | Streeter et al. |
| 6,893,460 | B2 | 5/2005 | Spenser et al. |
| 6,896,690 | B1 | 5/2005 | Lambrecht et al. |
| 6,908,481 | B2 | 6/2005 | Cribier |
| 6,913,600 | B2 | 7/2005 | Valley et al. |
| 6,929,653 | B2 | 8/2005 | Streeter |
| 6,931,286 | B2 * | 8/2005 | Sigg et al. ............ 607/120 |
| 6,936,066 | B2 | 8/2005 | Palmaz et al. |
| 6,939,365 | B1 | 9/2005 | Fogarty et al. |
| 6,951,571 | B1 | 10/2005 | Srivastava |
| 6,974,474 | B2 | 12/2005 | Pavcnik et al. |
| 6,974,476 | B2 | 12/2005 | McGuckin et al. |
| 6,986,742 | B2 | 1/2006 | Hart et al. |
| 6,986,784 | B1 * | 1/2006 | Weiser et al. ............ 623/1.1 |
| 6,989,027 | B2 | 1/2006 | Allen et al. |
| 6,989,028 | B2 | 1/2006 | Lashinski et al. |
| 6,991,649 | B2 | 1/2006 | Sievers |
| 7,018,401 | B1 | 3/2006 | Hyodoh et al. |
| 7,027,876 | B2 * | 4/2006 | Casavant et al. ............ 607/126 |
| 7,041,128 | B2 | 5/2006 | McGuckin, Jr. et al. |
| 7,044,966 | B2 | 5/2006 | Svanidze et al. |
| 7,048,014 | B2 | 5/2006 | Hyodoh et al. |
| 7,097,659 | B2 | 8/2006 | Woolfson et al. |
| 7,101,396 | B2 | 9/2006 | Artof et al. |
| 7,105,016 | B2 | 9/2006 | Shiu et al. |
| 7,115,141 | B2 | 10/2006 | Menz et al. |
| 7,128,759 | B2 | 10/2006 | Osborne et al. |
| 7,147,663 | B1 | 12/2006 | Berg et al. |
| 7,153,324 | B2 | 12/2006 | Case et al. |
| 7,160,319 | B2 | 1/2007 | Chouinard et al. |
| 7,175,656 | B2 | 2/2007 | Khairkhahan |
| 7,186,265 | B2 | 3/2007 | Sharkawy et al. |
| 7,195,641 | B2 | 3/2007 | Palmaz et al. |
| 7,198,646 | B2 | 4/2007 | Figulla et al. |
| 7,201,761 | B2 | 4/2007 | Woolfson et al. |
| 7,201,772 | B2 | 4/2007 | Schwammenthal et al. |
| 7,252,682 | B2 | 8/2007 | Seguin |
| 7,300,457 | B2 | 11/2007 | Palmaz |
| 7,300,463 | B2 | 11/2007 | Liddicoat |
| 7,316,706 | B2 | 1/2008 | Bloom et al. |
| 7,329,278 | B2 | 2/2008 | Seguin |
| 7,335,218 | B2 | 2/2008 | Wilson et al. |
| 7,338,520 | B2 | 3/2008 | Bailey et al. |
| 7,374,571 | B2 | 5/2008 | Pease et al. |
| 7,377,938 | B2 | 5/2008 | Sarac et al. |
| 7,381,218 | B2 | 6/2008 | Shreck |
| 7,384,411 | B1 | 6/2008 | Condado |

(56) References Cited

U.S. PATENT DOCUMENTS

| | | |
|---|---|---|
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,720,550 B2 * | 5/2010 | Sommer et al. ............... 607/127 |
| 7,824,704 B2 * | 11/2010 | Anderson et al. ............. 424/428 |
| 7,976,862 B2 * | 7/2011 | Anderson et al. ............. 424/428 |
| 8,021,680 B2 * | 9/2011 | Anderson et al. ............. 424/428 |
| 8,034,369 B2 * | 10/2011 | Anderson et al. ............. 424/428 |
| 8,099,177 B2 * | 1/2012 | Dahlberg ..................... 607/127 |
| 8,246,974 B2 * | 8/2012 | Chappa ........................ 424/423 |
| 8,623,049 B2 * | 1/2014 | Ward ........................... 606/232 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010481 A1 * | 1/2002 | Jayaraman ......... A61B 17/0057 606/151 |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099437 A1 * | 7/2002 | Anson ................ A61B 17/0057 623/1.15 |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehn |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |

(56) References Cited

U.S. PATENT DOCUMENTS

| | | |
|---|---|---|
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0131511 A1* | 6/2005 | Westlund ............... 607/126 |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0154252 A1* | 7/2005 | Sharkey et al. ............. 600/37 |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0047333 A1* | 3/2006 | Tockman et al. ............. 607/127 |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043415 A1* | 2/2007 | Junge et al. ............... 607/128 |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0067027 A1* | 3/2007 | Moaddeb et al. ............. 623/2.11 |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSeggesser et al. |

(56) References Cited

U.S. PATENT DOCUMENTS

| | | | |
|---|---|---|---|
| 2009/0192585 | A1 | 7/2009 | Bloom et al. |
| 2009/0192586 | A1 | 7/2009 | Tabor et al. |
| 2009/0192591 | A1 | 7/2009 | Ryan et al. |
| 2009/0198316 | A1 | 8/2009 | Laske et al. |
| 2009/0216310 | A1 | 8/2009 | Straubinger et al. |
| 2009/0216312 | A1 | 8/2009 | Straubinger et al. |
| 2009/0216313 | A1 | 8/2009 | Straubinger et al. |
| 2009/0234443 | A1 | 9/2009 | Ottma et al. |
| 2009/0240264 | A1 | 9/2009 | Tuval et al. |
| 2009/0240320 | A1 | 9/2009 | Tuval |
| 2009/0240326 | A1* | 9/2009 | Wilson et al. ............ 623/2.11 |
| 2009/0287296 | A1 | 11/2009 | Manasse |
| 2010/0030328 | A1* | 2/2010 | Seguin et al. ............ 623/2.11 |
| 2010/0036479 | A1 | 2/2010 | Hill et al. |
| 2010/0094411 | A1 | 4/2010 | Tuval et al. |
| 2010/0100167 | A1 | 4/2010 | Bortlein et al. |
| 2010/0131054 | A1 | 5/2010 | Tuval et al. |
| 2010/0137979 | A1 | 6/2010 | Tuval et al. |
| 2010/0161045 | A1 | 6/2010 | Righini |
| 2010/0234940 | A1 | 9/2010 | Dolan |
| 2012/0296417 | A1* | 11/2012 | Hill et al. ............ 623/2.11 |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. el61.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutancous Implantation of a Biological Valve in the Aorta to Treat Aortic Valve Insufficiency—A Sheep Study," Medical Science Monitor—International Medical Journal of Experimental and Clinical Research (Poland) Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutancous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

(56) References Cited

OTHER PUBLICATIONS

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation; Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, Edwards' United Kingdom action for invalidity, Claim No. HC 08CO0934 (83 pages).
Expert report of Dr. Nigel Buller, non-confidential annex—infringement, dated Jan. 12, 2009, Edwards' United Kingdom action for invalidity, Claim No. HC 08CO0934 (12 pages).
Expert report of Dr. Rodolfo Quijano, dated Jan. 9, 2009, Edwards' United Kingdom action for invalidity, Claim No. HC 08CO0934 (18 pages).
First Expert report of Prof. David Williams, dated Jan. 12, 2009, Edwards' United Kingdom action for invalidity, Claim No. HC 08CO0934 (41 pages).
First Expert report of Prof. Martin Rothman, dated Jan. 12, 2009, *Edwards Lifesciences and Cook Biotech*, Edwards' United Kingdom action for invalidity, Claim No. HC 08CO0934 (64 pages).
Fourth Expert report of Prof. Martin Rothman, dated Apr. 22, 2009, *Edwards Lifesciences and Cook Biotech*, Edwards' United Kingdom action for invalidity, Claim No. HC 08CO0934 (10 pages).
Second Expert report of Dr. Nigel Buller, dated Feb. 25, 2009, Edwards' United Kingdom action for invalidity, Claim No. HC 08CO0934 (24 pages).
Second Expert report of Dr. Rodolfo Quijano, dated Feb. 26, 2009, Edwards' United Kingdom action for invalidity, Claim No, HC 08CO0934 (6 pages).
Second Expert report of Prof. David Williams, dated Feb. 5, 2009, Edwards' United Kingdom action for invalidity, Claim No. HC 08CO0934 (15 pages).
Second Expert report of Prof. Martin Rothman, dated Feb. 5, 2009, *Edwards Lifesciences and Cook Biotech*, Edwards' United Kingdom action for invalidity, Claim No. HC 08CO0934 (11 pages).

Third Expert report of Dr. Nigel Buller, dated Apr. 21, 2009, Edwards' United Kingdom action for invalidity, Claim No. HC 08CO0934 (6 pages).
Third Expert report of Dr. Rudolto Quijano, dated Apr. 27, 2009 Edwards' United Kingdom action for invalidity, Claim No. HC 08CO0934 (3 pages).
Third Expert report of Prof. David Williams, dated Apr. 22, 2009, Edwards' United Kingdom action for invalidity, Claim No. HC 08CO0934 (9 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Dr. Anthony C. Lunn (7 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Witness statement of Stanton Rowe (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Witness statement of Stanton Rowe (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
PVT slides naming Alain Cribier, Martin Leon, Stan Rabinovich and Stanton Rowe (16 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Expert Rebuttal Report of Prof. Martin T. Rothman (32 pages) redacted, *Edwards v. CoreValve*, U.S. District Court, District of Delaware, Case No. 08-091, dated Jul. 29, 2009.
Expert Report of Prof. Martin T. Rothman (74 pages) redacted, *Edwards v. CoreValve*, U.S. District Court, District of Delaware, Case No. 08-091, dated Jun. 29, 2009.
First Expert report of Richard A. Hillstead (41 pages), *Corevalve, Inc. v. Edwards Lijesciences AG and Edwards Lifesciences PVT, Inc.*, High Court of Justice—Chancery Division Patents Court, United Kingdom, Case No. HC-07-C01243.
Reply Expert report of Richard A. Hillstead (9 pages), *Corevalve, Inc. v. Edwards Litesciences AG and Edwards Lifesciences PVT, Inc.*, High Court of Justice—Chancery Division Patents Court, United Kingdom, Case No. HC-07-C01243.

\* cited by examiner

IMPLANT FOR TREATMENT OF A HEART VALVE, IN PARTICULAR A MITRAL VALVE, MATERIAL INCLUDING SUCH AN IMPLANT, AND MATERIAL FOR INSERTION THEREOF

The present invention concerns an implant for treatment of a heart valve, in particular a mitral valve of a heart, a material including such an implant and a material for insertion thereof. The treatment in question may consist of performing an annuloplasty, i.e. reducing a distension of the annulus, or strengthening the annulus of a normal valve. The invention also concerns a percutaneous intervention method for performing such a treatment.

The annulus of a heart valve can, over time, undergo a distension leading to poor coaptation of the leaflets, resulting in a loss of sealing of the valve.

To treat this affection, it is well known to perform an annuloplasty, i.e. re-calibration of the annulus using an implant inserted on the valvular annulus.

This annuloplasty implant can be a prosthetic annulus fixed on the native valvular annulus. This technique does, however, have the drawback of involving an open-heart operation.

The annuloplasty implant can also be a deformable elongated member, able to be introduced using a catheter through a minimally-invasive vascular approach, then able to be delivered via the catheter and fixed near the valvular annulus before being circumferentially retracted.

The existing annuloplasty implants of this type, and the corresponding implantation techniques, like the systems using the coronary sinuses, are not, however, fully satisfactory.

One existing implant, described by document N° WO 2006/091163, is formed by a helically wound wire, forming a split annulus having dimensions close to those of the valvular annulus. This implant is designed to be engaged on the base of the leaflets and to grip this base.

Moreover, it may be necessary to implant a prosthetic heart valve, in particular percutaneously using a catheter. Currently, this type of implantation is difficult on the mitral valve of a heart, percutaneously, essentially due to the fact that the annulus of a mitral valve is elastic and risks becoming distended upon percutaneous implantation of a prosthetic valve.

The present invention essentially aims to resolve the drawbacks and gaps of the prior art.

This implant is, in a known manner, made up of a helically-wound wire.

To this end, the implant according to the invention
has dimensions such that it is able to be screwed into the wall of the annulus and/or into the cardiac wall adjoining this annulus such that one portion of this annulus and/or of this wall is located in the perimeter of the implant; and
comprises at least one coil able, during said screwing of the implant, to be inserted in said wall while having a first dimension and at least one second coil having a second dimension, or adopting this second dimension after implantation, said second dimension being smaller than the first dimension such that the implant, once inserted, enables a contraction of said wall portion located in the perimeter of this implant.

The implant according to the invention thus has much smaller dimensions than those of the annulus of the valve to be treated, such that it can be placed locally in the wall of this annulus and/or in the cardiac wall adjoining this annulus. By "much smaller dimensions", one must understand that the implant has, in the plane perpendicular to its screwing axis, a maximum dimension at most equal to 15 mm, and generally in the vicinity of 10 mm, or smaller than 10 mm. This implant can have circular coils; said first coil(s) then have an external diameter of at most 15 mm. The implant can also have elliptical coils; said first coils then have a dimension of at most 15 mm along their largest axis.

"Screwing of the implant" designates a rotation of the implant along its axis, done so as to cause the helical coil formed by this implant to move in a direction. Below, the terms "front" and "rear" will designate the parts of the implant located on the front side or the rear side, respectively, in relation to the direction of screwing.

The implant is simply placed in the annulus and/or the cardiac wall, along a direction more or less perpendicular to the plane of the annulus, and makes it possible to achieve a local contraction of the tissue constituting this annulus and/or this wall. This contraction performs, in whole or in part, the annuloplasty. The radial contraction thus done also allows local strengthening of the annulus.

When said radial contraction only partially performs the aforementioned annuloplasty and/or strengthening, a plurality of implants according to the invention can be inserted closer and closer on the annulus and/or the wall, or on a portion of this annulus and/or this wall, to perform all of the desired annuloplasty and/or strengthening.

According to one possible formation of the coils, said first coil(s) are located, in the direction of screwing of the implant, in front of said second coil(s).

During screwing of the implant, said first coil(s) penetrate first into the annulus and/or the cardiac wall and form a path having corresponding dimensions, which will then be used by said second coil(s), of smaller dimensions, thereby bringing about the radial contraction of said portion of the annulus and/or wall.

The coils of the implant can be circular, as already mentioned, or have a non-circular shape, in particular oval or elliptical.

The implant performs an additional contraction of the annulus and/or of said adjoining wall according to its angular position in this annulus and/or this wall.

According to another possible formation of the coils, the wire making up the implant is in a shape memory material, defining, in a first state, coils having said first dimension and, in a second state, coils having said second dimension.

The passage of these coils from said first dimension to said second dimension, by shape memory, causes the contraction of said portion of the annulus located in the perimeter of these coils of the implant.

The possible formations of the coils mentioned above can be combined on a same implant. Thus, for example, an implant can comprise at least one coil having a larger diameter and at least one coil having a smaller diameter, and be in a shape memory material such that the diameter of the coils is reduced after implantation; an implant can be in a shape memory material such that it comprises circular coils at the time of its implantation, assuming a non-circular shape after implantation.

The front end of the wire constituted by the implant is preferably pointed or sharp, so as to facilitate its penetration into the tissue of the annulus and/or said cardiac wall.

The wire constituting the implant can have a same structure along its entire length, or comprise portions in a first material and portions in a second material different from the first material. For example, the implant can comprise portions in non-shape memory wire and portions in shape memory wire; the implant can comprise portions of wire in a non-resorptive material and portions of wire in a resorptive material.

The wire constituting the implant can for example be in stainless steel or in a shape memory material such as an alloy of nickel and titanium known by the name "nitinol", or in a material using superelasticity, or in a resorptive material.

The wire constituting the implant can also comprise portions of different structures, for example solid, resistant portions and portions having a thinner cross-section able to be broken in the event of radial forces directed toward the exterior. In this second case, the implant can, for example, be used on children, and break under the effort of said stresses resulting from the growth of the patient.

The implant can comprise radiopaque markers enabling its visualization through the patient's body, in particular markers enabling visualization of the angular orientation of the implant when the latter comprises non-circular coils.

The implant can also comprise means ensuring its anchoring in the tissue with regard to screwing or unscrewing; for example, a rear portion of the wire can, by shape memory, bore itself in such that the wire can no longer slide in relation to the tissue in which the implant is placed; the implant can also comprise protruding portions, for example in the form of claws, deploying via shape memory.

The material including the implant according to the invention comprises means making it possible to connect at least two adjacent implants placed in an annulus, so as to achieve a contraction of the wall of the annulus located between the implants, in addition to the contraction achieved by the implants themselves. It can in particular involve wires in a material able to be twisted, in particular in a metallic material, connected to the proximal parts of the implants, these wires being engaged in a same catheter then being twisted in order to bring the two implants closer together.

It can also involve wires or strips in metal or in a material using superelasticity, or a shape memory material connecting two implants, able to be shortened after implantation.

The material for insertion of an implant according to the invention includes at least one catheter able to deliver the implant, means for longitudinal movement of the implant in relation to this catheter and means for driving the implant in rotation along the axis of the implant.

The material according to the invention thus enables precise insertion of the implant, using a minimally-invasive approach.

The longitudinal movement means may comprise a push-rod slidingly engaged in the catheter.

The rotational driving means may comprise a wire separably connected to the rear end of the implant.

The separability of the wire connected to the rear end of the implant can in particular be achieved via a removable connection of this wire and this end, in particular using an assembly via reversible locking, being released via traction on the wire.

The percutaneous intervention method according to the invention comprises the steps consisting of:
  using the implant and the material as mentioned above;
  bringing the distal opening of the catheter comprised by the material across from the area designed to receive the implant;
  causing the implant to move forward in relation to the catheter while driving this implant in rotation along its axis, in order to perform screwing of the implant into the annulus of the valve to be treated and/or the cardiac wall adjoining this annulus;
  if needed, repeat the preceding steps so as to insert as many implants as necessary to perform the desired annuloplasty and/or the strengthening of the annulus.

The step consisting of bringing the distal opening of the catheter across from the area designed to receive the implant may be done by approaching the valve via one or the other of the sides of this valve, in particular, involving the treatment of a mitral valve, either via a ventricular approach or an auricular approach.

The invention will be well understood, and other characteristics and advantages thereof will appear, in reference to the appended diagrammatic drawing, illustrating, as non-limiting examples, several possible embodiments of the implant and the material it concerns.

FIG. 1 illustrates an implant 1 for treatment of a heart valve, in particular a mitral valve of a heart, this treatment being able to consist of performing an annuloplasty, i.e. reducing a distension of the annulus, or strengthening the annulus of a normal valve.

Figure 1:
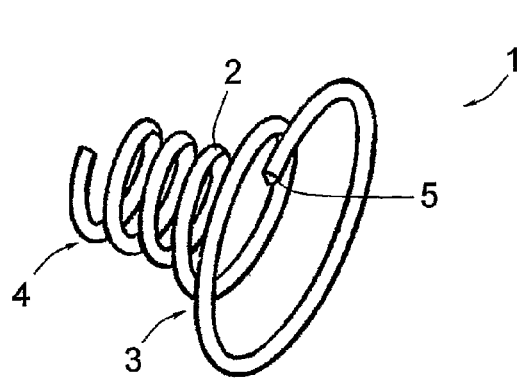
FIG. 1 is a perspective view of the implant according to a first embodiment.

As illustrated, the implant 1 is formed by a helically wound wire 2 and comprises a conical portion 3 and a cylindrical portion 4. The wound wire 2 forms a plurality of complete coils, where each complete coil is one 360 degree revolution along the helical or spiral shape of the wound wire 2. The conical portion 3 generates complete coils or complete 360 degree revolutions whereof the diameter continuously decreases in the direction of the cylindrical portion 4, which is formed by complete coils having a constant diameter. The conical portion 3 can include at least two complete coils or 360 degree revolutions of continuously decreasing diameter from end 5 as shown in FIG. 1.

The end 5 of the wire 2 at the level of the coil having the largest diameter of the conical portion 3 is pointed, so as to be able to pierce the tissue constituting the annulus of a mitral valve and/or the wall of the ventricle adjoining this annulus.

Figure 2:
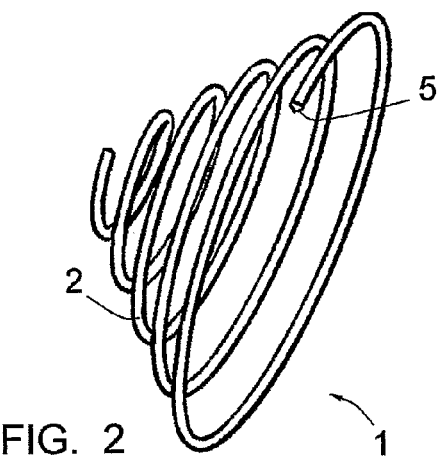
FIG. 2 is a perspective view of the implant according to a second embodiment.

FIG. 2 illustrates an implant 1 having a similar structure but having a purely conical shape, i.e. comprising coils whereof the diameter decreases from one end of the implant to the other.

Figure 3:
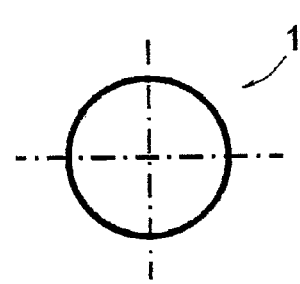
FIG. 3 is a flat diagrammatic view of a coil of the implant.
Figure 4:
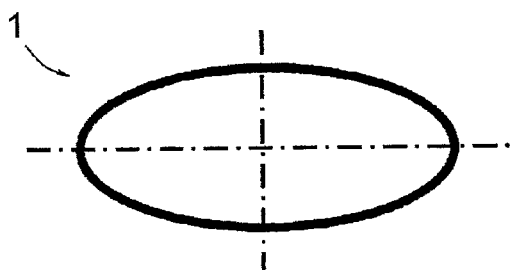
FIG. 4 is a flat diagrammatic view of a coil of another implant.

FIG. 3 shows that the implant 1 can have circular coils and FIG. 4 shows that the implant 1 can comprise coils having an elliptical shape.

FIGS. 5 to 10 show one possible procedure for inserting one or the other of the aforementioned implants 1.

During a first step, a catheter containing a hollow piercing needle is introduced via the aorta 100, up to the left ventricle 101 then is engaged between the pillars 102 until the distal end of the catheter arrives against the ventricular wall in the immediate vicinity of the annulus 103 of the mitral valve. To follow this journey, the catheter can present appropriate successive curves or can be of the "deflectable" type, i.e. able to be oriented using sliding wires which it comprises in its wall.

Once this catheter is in place, the needle is deployed to pierce the ventricular wall, and a guide wire 10 is slid through this needle to the inside of the left auricular appendix 104.

Figure 5:
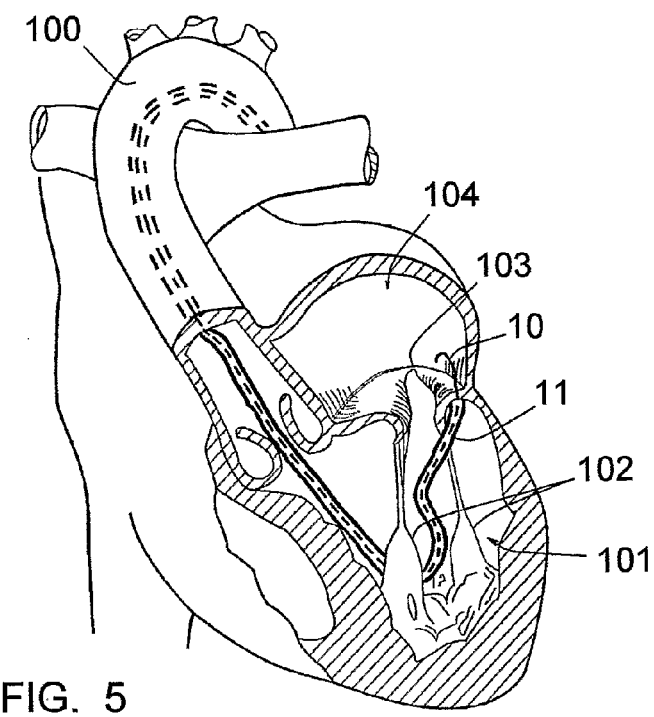
FIG. 5 is a view of a heart in partial cross-section, during a first step of insertion of the implant according to the invention.

The catheter is then removed while still keeping the wire 10 in place, and another catheter 11, containing the implant 1, is slid on the wire 10 until its distal opening is in the immediate vicinity of the mitral annulus 103, as shown by FIG. 5.

Figure 6:
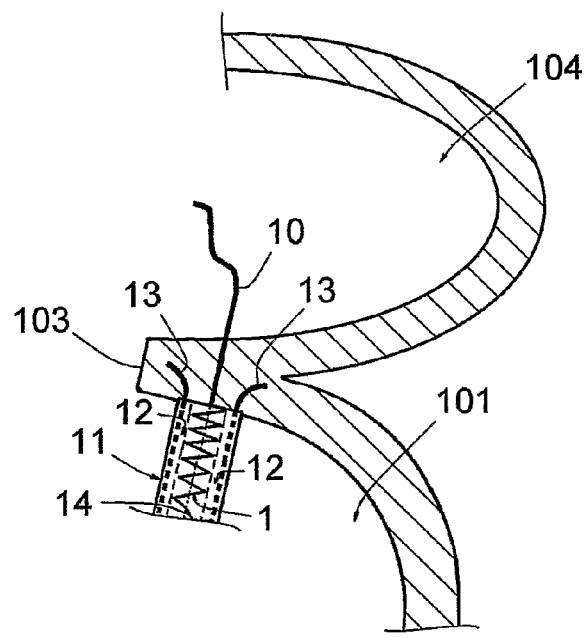
FIGS. 6 to 9 are views of four successive steps for insertion of the implant.
Figure 7:
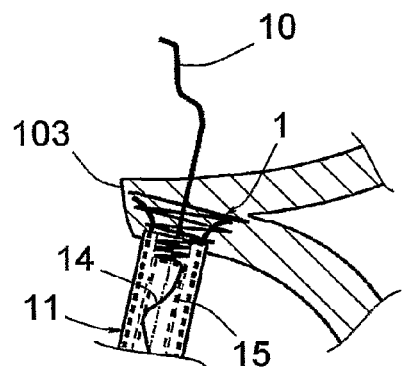
Figure 8:
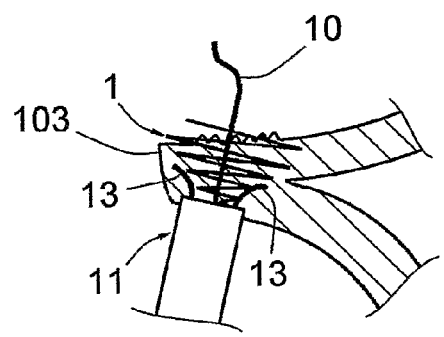
Figure 9:
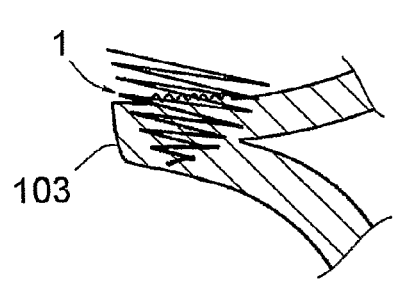

It appears in FIG. 6 that this catheter 11 comprises two diametrically opposed ducts 12 wherein are engaged and can slide two wires 13 whereof the distal ends are bent. These distal ends are elastically deformable such that they can adopt a substantially rectilinear shape enabling the wires 13 to slide in the ducts 12, and resume their neutral curved shape when they are outside these ducts 12.

Once the distal end of the catheter 11 is in contact with the ventricular wall, these distal ends are deployed outside the ducts 12 and penetrate inside this ventricular wall, ensuring that the catheter 11 is kept in position.

The implant 1 is contained in its stressed state in the catheter 11, and its rear end is removably connected, by reversible locking, to a wire 14. This wire 14 is engaged through a radially offset opening 15 comprised by the distal end wall of a hollow push-rod 16 engaged in the catheter 11, this push-rod 16 being able to pivot in the lumen of the catheter 11.

Figure 12:
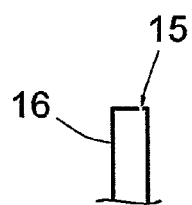
FIG. 12 is a side view of a push-rod comprised by the material according to the invention.
Figure 13:
FIG. 13 is an end view of this push-rod.

FIGS. 12 and 13 more particularly show the push-rod 16 and its opening 15.

The push-rod 16 is used to screw the implant 1 into the ventricular wall, i.e. to move this implant 1 longitudinally in relation to the catheter 11 so as to remove the latter while driving it in rotation around its axis. During this screwing, the first coil having the largest diameter first penetrates the ventricular wall and forms a path corresponding to its diameter, which will then be used by the following coil of smaller diameter, and so on (cf. FIGS. 7 and 8). Each coil of smaller diameter then produces a radial contraction of the portion of the ventricular wall located in the perimeter of the path pierced by the first coil. This contraction thus makes it possible to reduce the diameter of the annulus 103, performing, in whole or in part, an annuloplasty and/or a local strengthening of the annulus.

When the implant 1 is completely screwed into the ventricular wall, the push-rod 16 is removed and the wire 14 is separated from the implant 1, by traction so as to release the reversible locking whereby this wire 14 is connected to the implant 1. The wires 13 are then retracted, and the catheter 11 and then the guide wire 10 are removed (cf. FIGS. 9 and 10).

Figure 10:
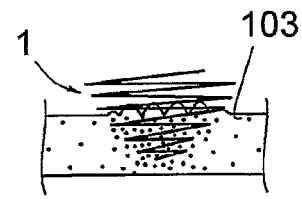
FIG. 10 is a view of the implant along a direction perpendicular to FIG. 9.
Figure 11:
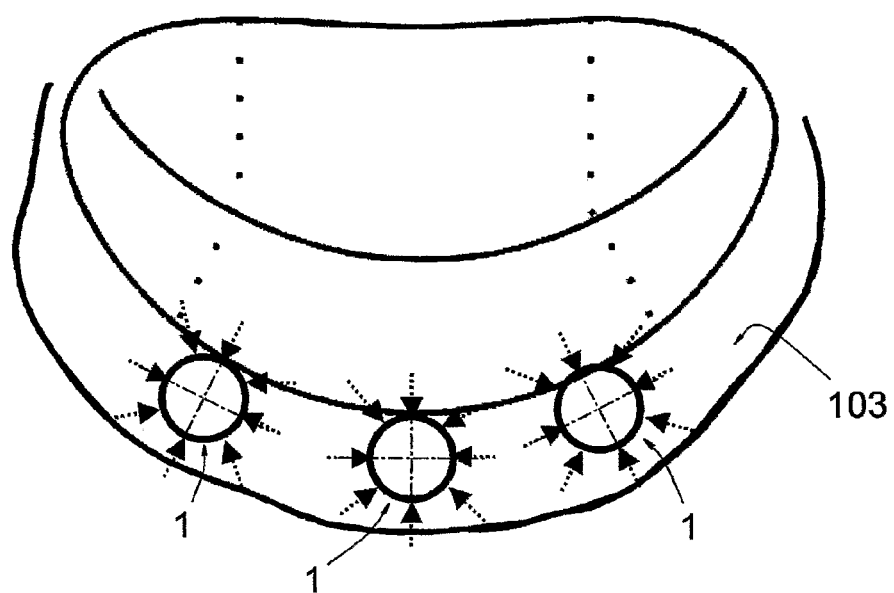
FIG. 11 is an outline sketch of a mitral valve in which three implants have been inserted.

When required by the annuloplasty to be performed, several implants are inserted side by side, in particular three implants in the example shown in FIG. 10.

The wire 2 can be made of a shape memory material such that the coils it forms can naturally go outside the catheter 11 during forward progress of an implant 1 outside this catheter 11.

Figure 14:
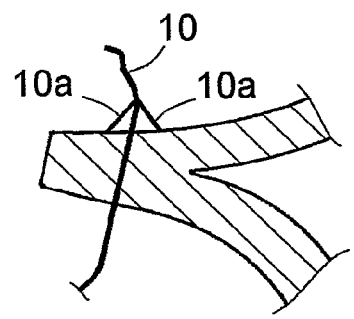
FIG. 14 is a view of one variation of embodiment of the material according to the invention.

FIG. 14 shows that the wire 10 can comprise branches 10a deployable by elasticity or shape memory, which make it possible to produce a certain retention of this wire 10 in the auricular appendix 104. These branches 10a can, however, pivot from the side of the free end of the wire 10 when tension is exerted on the latter, such that the removal of this wire remains possible.

Figure 15:
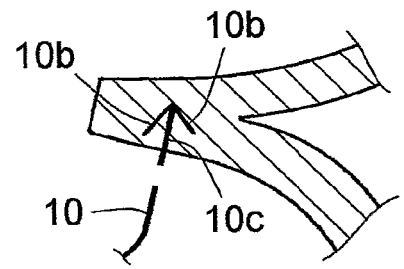
FIG. 15 is a view of another variation of embodiment of the material according to the invention.

FIG. 15 shows that, according to another embodiment of the invention, the wire 10 comprises deployable branches 10b, enabling anchoring of a distal portion 10c of the wire 10 in the ventricular wall, this distal portion 10c being separably connected, in particular by reversible locking, to the rest of the wire 10. This distal portion 10c remains in place after insertion of the implant 1.

Figure 16:
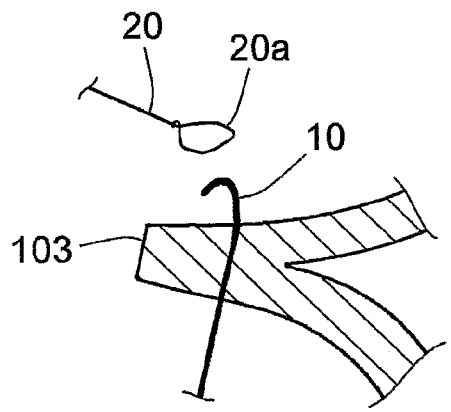
FIGS. 16 and 17 are still further views of another variation of embodiment of the material according to the invention.
Figure 17:
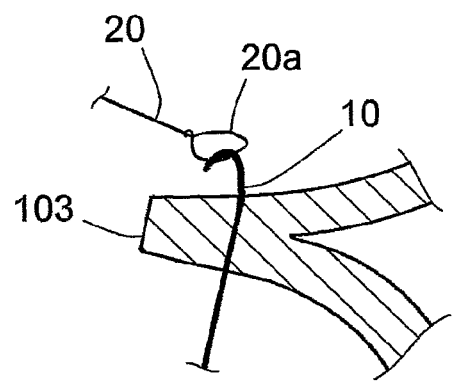

FIGS. 16 and 17 show that the implant 1 can be inserted via the auricular side of the mitral valve. The wire is "captured" according to the so-called "lasso" technique by the loop 20a of another wire 20, introduced using a transseptal approach. The wire 10 is then pulled to allow guiding of the catheter 11 by the same transseptal approach, and placement of the implant 1 using a technique similar to that previously described.

Figure 18:
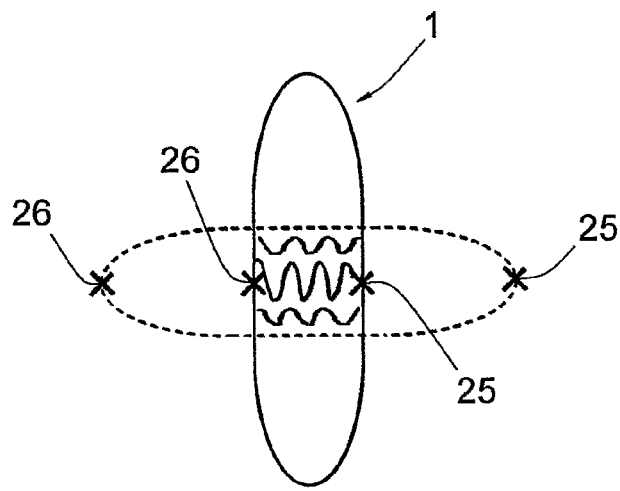
FIG. 18 is a view of another embodiment of the implant according to the invention.
Figure 19:
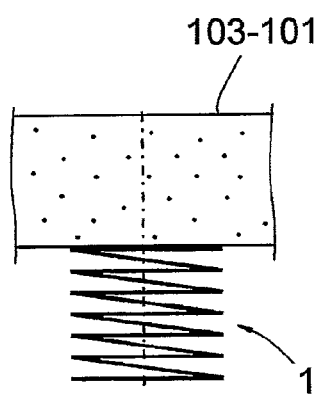
FIGS. 19 to 22 are views of yet another embodiment of the implant according to the invention, during four successive steps of insertion.
Figure 20:
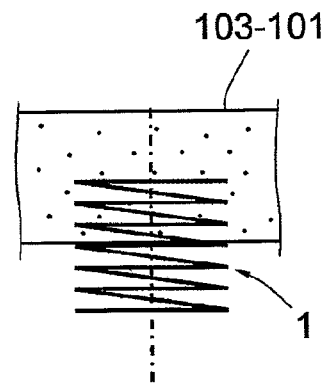
Figure 21:
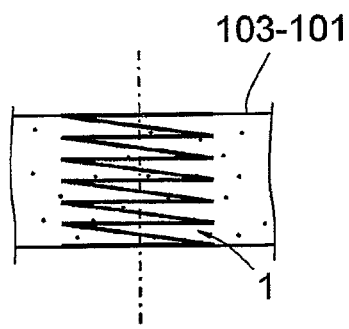
Figure 22:
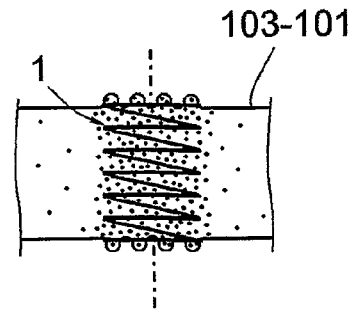
Figure 23:
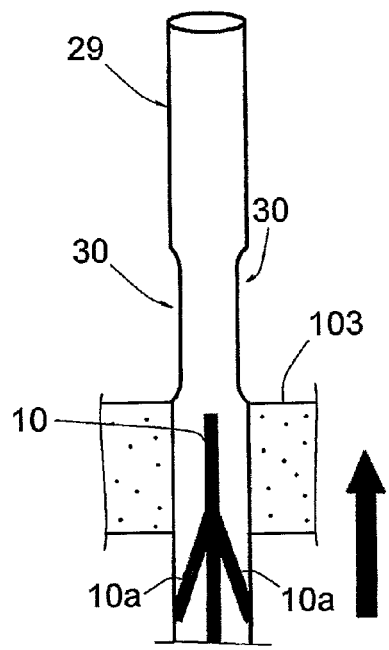
FIGS. 23 to 30 are views of yet another embodiment of the material according to the invention.
Figure 24:
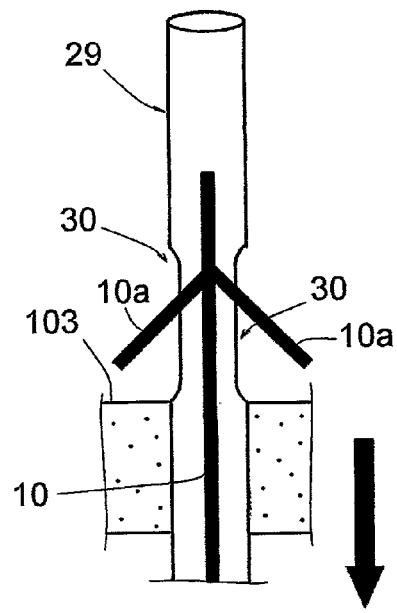
Figure 25:
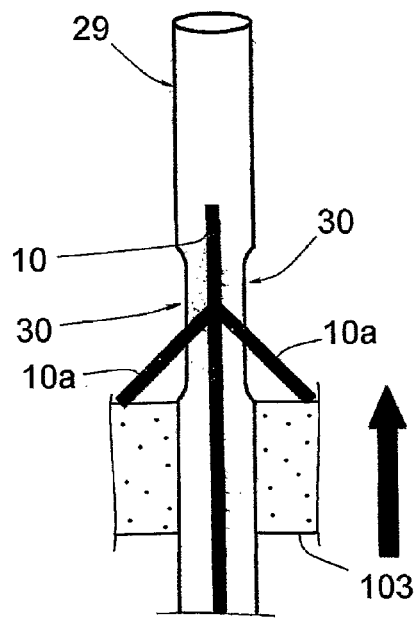
Figure 26:
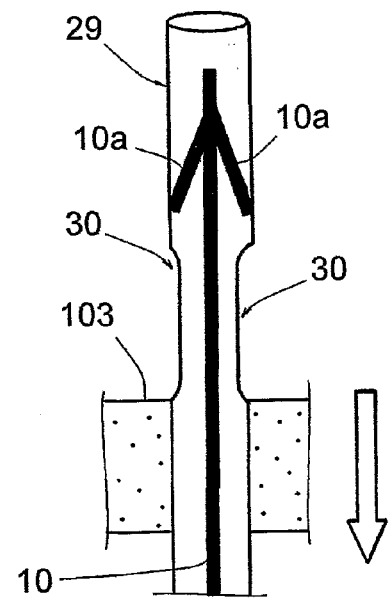

FIG. 18 shows, very diagrammatically, a helical implant 1 whereof the coils have a flat ellipsoidal shape. As is understood, each coil defines, in the implantation tissue, a path going through points 25, 26 separated from each other (cf. first angular position illustrated in broken lines); when the implant 1 is rotated a quarter turn (cf. second angular position shown in solid line), the two points 25, 26 are brought closer together, producing the contraction of the tissue located in the central perimeter of the implant.

FIGS. 19 to 22 illustrate an implant 1 having a cylindrical shape, i.e. having coils of a constant diameter, which is made of a shape memory material. After placement of the implant 1 by screwing (cf. FIGS. 18 to 20), a calorific contribution takes place, in particular through the implementation of a difference in potential between the implant and the patient's body. This calorific contribution produces, via shape memory, a reduction in the diameter of the coils of the implant 1, and therefore a contraction of the portion of the wall located in the perimeter of the implant 1.

FIGS. 23 to 26 show another embodiment of the material for inserting the implant 1, wherein the aforementioned hollow piercing needle 29 has lateral lumens 30 arranged through its wall, and wherein the wire 10 is equipped with deployable branches 10a as described above. While the wire 10 is positioned in the needle 29 such that the branches 10a are outside the area of the lumens 30, the needle 29 is introduced through the annulus 103 and is positioned such that its lumens 30 are located beyond the wall of the annulus 103 (cf. FIG. 23); the wire 10 is then slid in the needle 29 to bring the branches 10a across from the lumens 30, which allow deployment of the branches 10a (cf. FIG. 24), then these are brought into contact with the wall of the annulus 103 (cf. FIG. 25); for removal of the wire 10, this wire is slid in relation to the needle 29 until it brings the branches 10a into the portion of this needle located beyond the lumens 30 from the distal side, thereby achieving bending of the branches 10a in the needle 29 and thus allowing removal thereof by sliding.

Figure 27:
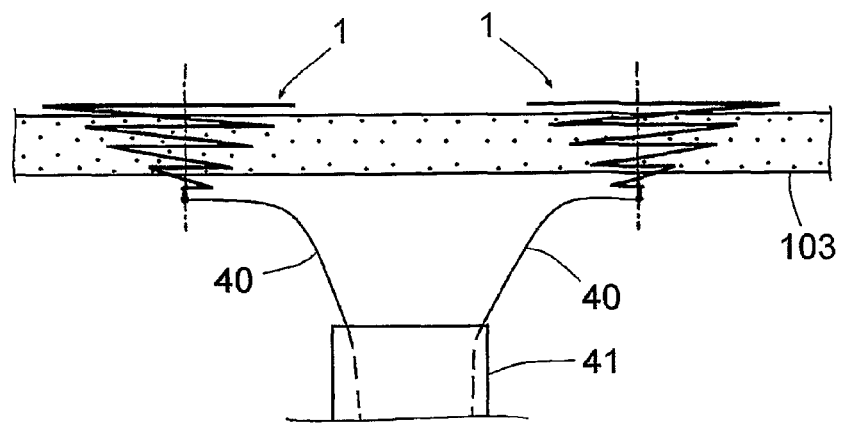
Figure 28:
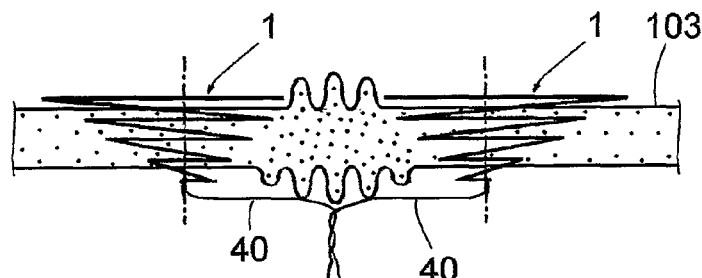

FIG. 27 shows that, according to one particular embodiment of the invention, the proximal ends of two adjacent implants 1 can be connected to wires 40 engaged in a catheter 41. These wires 40 are in a relatively stiff material able to be twisted, in particular in metal. Tension exerted on the wires 40, then twisting of said wires, produces a contraction of the wall of the annulus 103 located between the implants 1, in addition to the contraction produced by the implants 1 themselves, as shown by FIG. 28. Each wire 40 can in particular be connected to a loop formed by the proximal end of each implant 1, before insertion of the implant.

Figure 29:
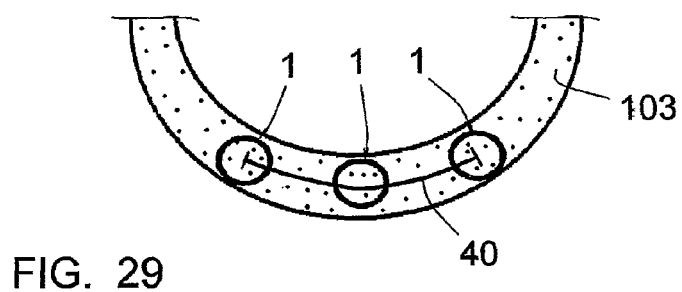
Figure 30:
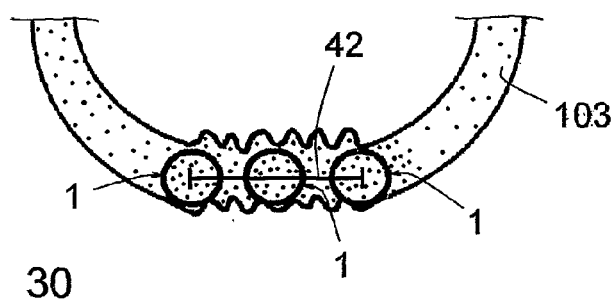

FIGS. 29 and 30 show the principle of a connection element 42 having a curved shape, able to connect three implants 1. This connection element 42 can go from a first bend, which it has before implantation, to a smaller or rectilinear bend, which it has after implantation, so as to reduce the bend of the portion of the annulus 103 located between the implants.

The connection element 42 can also go, via shape memory, from an elongated shape before implantation to a shortened shape after implantation, in order to produce a contraction of the annulus 103 due to the three implants coming closer together. This connection element 42 thus forms a stiffener.

Figure 31:
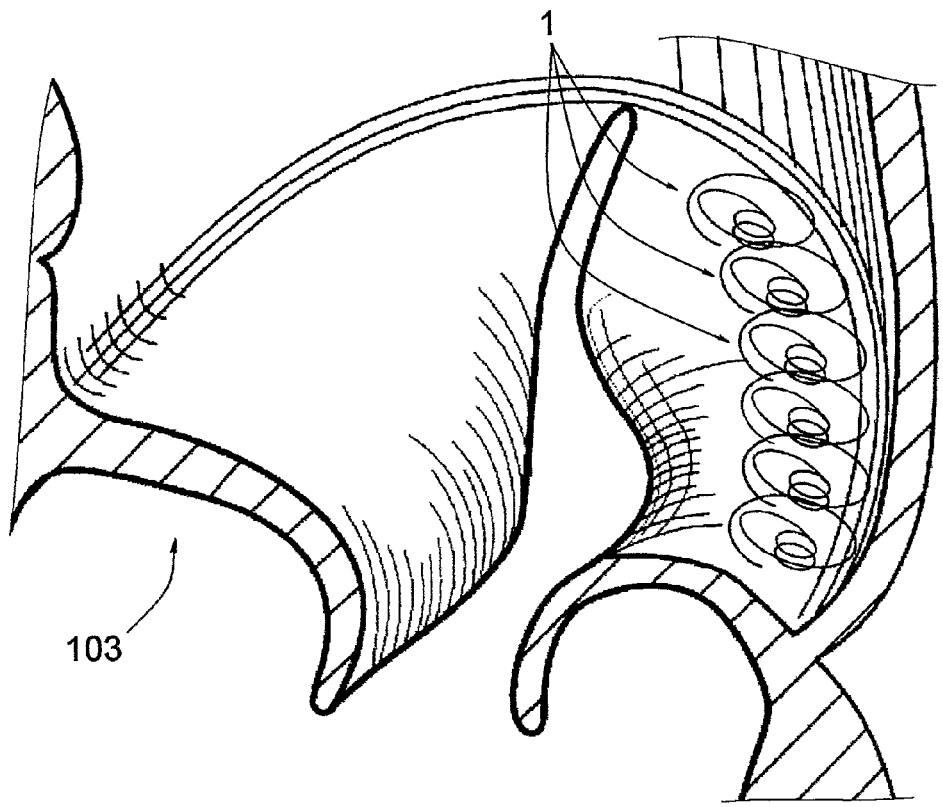
FIG. 31 is a partial perspective view of a heart annulus having a series of implants according to another embodiment, placed in its wall.
Figure 32:
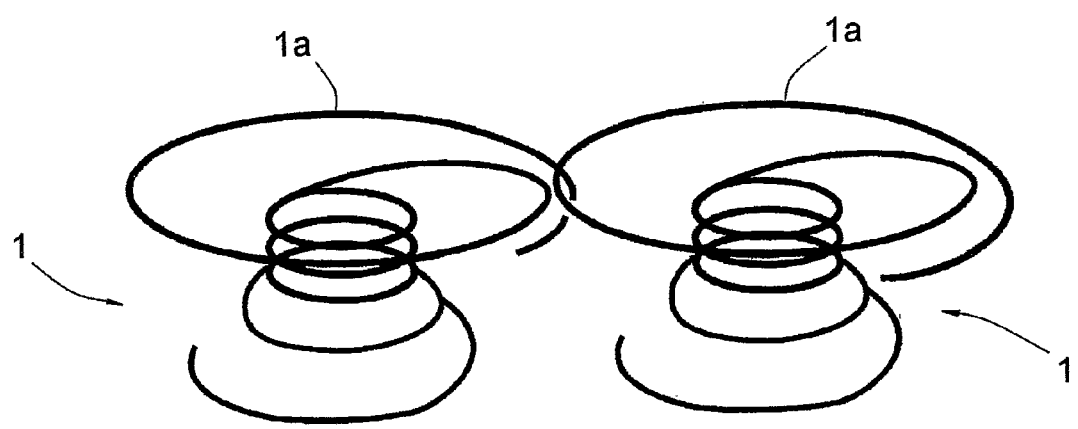
FIG. 32 is an enlarged perspective view of two implants from this series of implants.

FIGS. 31 and 32 show that an implant 1 can comprise a front coil 1a of large diameter, and that the coils 1a of several implants 1 can be interconnected upon insertion of several consecutive implants, connecting these implants to each other.

As appears from the preceding, the invention provides an implant for treating a heart valve, in particular a mitral valve of a heart, and a material for inserting this implant, which is completely satisfactory and which makes it possible to perform either annuloplasties or strengthening of valvular annuluses, under the best possible conditions. This implant and this material consequently have determining advantages in relation to the existing techniques.

It goes without saying that the invention is not limited to the embodiment described above as an example, but that it extends to all embodiments covered by the appended claims.

The invention claimed is:

1. Implant for treating a heart valve, in particular a mitral valve of a heart, the implant comprising:
   a helically wound wire capable of insertion into a wall of an annulus and/or a cardiac wall adjoining the annulus, the helically wound wire further comprising:
   a conical portion comprising at least one complete coil, each complete coil being one 360 degree revolution of the wound wire, each complete coil of the conical portion having a continuously decreasing diameter from a pointed end for insertion to a non-pointed end of the conical portion, the conical portion capable of insertion into the wall such that a portion of the wall is located within the respective diameter of at least one complete coil and contracted during insertion of the conical portion; and
   a cylindrical portion attached to the non-pointed end of the conical portion, the cylindrical portion terminating at a terminal non-pointed end opposite the pointed end of the conical portion such that the helically wound wire extends between and terminates at the pointed end of the conical portion and the terminal non-pointed end of the cylindrical portion, the cylindrical portion further maintaining contraction of the portion of the wall located within the diameter of the cylindrical portion during implantation of the cylindrical portion.

2. Implant according to claim 1, characterized in that the conical portion is located, in the direction of screwing of the implant, in front of the cylindrical portion.

3. Implant according to claim 1, characterized in that the wire constituting the implant is in a shape memory material, defining, in a first state, complete coils having a first diameter and, in a second state, complete coils having a second diameter.

4. Implant according to claim 1, characterized in that the wire has a same structure along its entire length.

5. Implant according to claim 1, characterized in that the wire comprises the conical portion constructed from a first material and the cylindrical portion constructed from a second material different from the first material.

6. Implant according to claim 1, characterized in that the wire comprises the conical and cylindrical portions having different structures, for example solid, resistant portions and portions having a thinner cross-section able to break in case of exertion on the implant of stresses directed radially outwardly.

7. Implant according to claim 1, characterized in that the implant further comprises radiopaque markers enabling visualization of portions of the implant through the body of the patient, in particular markers capable of visualizing an angular orientation of the implant when the implant comprises non-circular coils.

8. Implant according to claim 1, characterized in that the implant further comprises means ensuring anchoring of the implant in the tissue with regard to screwing or unscrewing.

9. Implant according to claim 1, characterized in that the cylindrical portion comprises coils of a consistent diameter.

10. Implant according to claim 1, characterized in that the conical portion comprises at least two complete coils of continuously decreasing diameter from the pointed end.

11. Implant for treating a heart valve, in particular a mitral valve of a heart, made up of a helically wound wire, characterized in that:
   it has dimensions such that it can be screwed into a wall of an annulus and/or into cardiac wall adjoining the annulus so that a portion of the annulus and/or of the wall is located in a perimeter of the implant; and
   the implant comprises a plurality of complete coils, each complete coil being one 360 degree revolution of the wound wire, the plurality of complete coils including a first complete coil constructed from a first material and terminating at a pointed end for insertion, the first complete coil able, upon screwing of the implant, to insert itself into the wall and having a first continuously decreasing diameter from the pointed end, wherein the plurality of complete coils includes a second complete coil constructed from a second material different from the first material and terminating at a non-pointed end opposite the pointed end such that the implant extends between and terminates at the pointed end and the non-pointed end of the implant, the second complete coil having a second diameter;
   after implantation, the second diameter being smaller than the first decreasing diameter such that the implant, once inserted, allows contraction of the wall portion located in the perimeter of the implant.

* * * * *